United States Patent
Ashrafi et al.

(10) Patent No.: US 10,351,105 B2
(45) Date of Patent: Jul. 16, 2019

(54) ILLUMINATION FOR DETECTING RAINDROPS ON A PANE BY MEANS OF A CAMERA

(71) Applicant: Conti Temic microelectronic GmbH, Nuremberg (DE)

(72) Inventors: Mina Ashrafi, Neu-Ulm (DE); Stefan Bix, Baindt (DE)

(73) Assignee: Conti Temic microelectronic GmbH, Nuremberg (DE)

( * ) Notice: Subject to any disclaimer, the term of this patent is extended or adjusted under 35 U.S.C. 154(b) by 308 days.

(21) Appl. No.: 15/102,146

(22) PCT Filed: May 5, 2014

(86) PCT No.: PCT/DE2014/200196
§ 371 (c)(1),
(2) Date: Jun. 6, 2016

(87) PCT Pub. No.: WO2015/081934
PCT Pub. Date: Jun. 11, 2015

(65) Prior Publication Data
US 2016/0339873 A1    Nov. 24, 2016

(30) Foreign Application Priority Data

Dec. 6, 2013 (DE) .................. 10 2013 225 155

(51) Int. Cl.
*G06K 9/00* (2006.01)
*B60S 1/08* (2006.01)
(Continued)

(52) U.S. Cl.
CPC ........ *B60S 1/0844* (2013.01); *G01N 21/4738* (2013.01); *G01N 21/552* (2013.01);
(Continued)

(58) Field of Classification Search
None
See application file for complete search history.

(56) References Cited

U.S. PATENT DOCUMENTS 5,923,027 A * 7/1999 Stam ................ B60S 1/0822
250/208.1
6,020,704 A    2/2000 Buschur
(Continued)

FOREIGN PATENT DOCUMENTS

DE  202004015345    5/2005
DE  102006008274    8/2007
(Continued)

OTHER PUBLICATIONS

International Search Report of the International Searching Authority for International Application PCT/DE2014/200196, dated Aug. 7, 2014, 3 pages, European Patent Office, HV Rijswijk, Netherlands.
(Continued)

*Primary Examiner* — Chikaodili E Anyikire
(74) *Attorney, Agent, or Firm* — W. F. Fasse

(57) ABSTRACT

A device for detecting rain on a pane includes a camera, a lighting source for emitting light and a diffusion element. The light emitted by the lighting source is diffused through and emerges as a light sheet from the diffusion element. The camera, the lighting source and the diffusion element are configured and arranged so that the camera can detect a signal from an image of the light sheet that is emitted by the lighting source, diffused through the diffusion element, impinges on the pane and is reflected or scattered by the pane and/or a raindrop on the pane. The signal detected by the camera is evaluated to detect whether there is rain on the pane.

18 Claims, 2 Drawing Sheets

(51) Int. Cl.
*G01N 21/552* (2014.01)
*G01N 21/47* (2006.01)
*H04N 5/225* (2006.01)
*G01N 21/43* (2006.01)

(52) U.S. Cl.
CPC ....... *G06K 9/00791* (2013.01); *H04N 5/2253* (2013.01); *H04N 5/2256* (2013.01); *G01N 2021/435* (2013.01); *G01N 2021/4764* (2013.01); *G01N 2201/062* (2013.01); *G01N 2201/068* (2013.01)

(56) References Cited

U.S. PATENT DOCUMENTS

| | | | |
|---|---|---|---|
| 7,253,898 | B2 | 8/2007 | Saikalis et al. |
| 7,259,367 | B2 | 8/2007 | Reime |
| 7,855,353 | B2 | 12/2010 | Blaesing et al. |
| 8,792,174 | B2 | 7/2014 | Schmaelzle et al. |
| 9,120,464 | B2 | 9/2015 | Pack et al. |
| 9,335,264 | B2 | 5/2016 | Kroekel et al. |
| 2002/0148987 | A1 | 10/2002 | Hochstein |
| 2005/0178954 | A1 | 8/2005 | Yukawa |
| 2005/0206511 | A1 | 9/2005 | Heenan et al. |
| 2006/0076477 | A1 | 4/2006 | Ishikawa |
| 2006/0076478 | A1* | 4/2006 | Johnson ............... B60S 1/0822 250/227.25 |
| 2008/0129206 | A1 | 6/2008 | Stam et al. |
| 2010/0053613 | A1* | 3/2010 | Taoka ............... B60S 1/0837 356/342 |
| 2010/0208060 | A1 | 8/2010 | Kobayashi et al. |
| 2011/0031921 | A1 | 2/2011 | Han |
| 2011/0204206 | A1 | 8/2011 | Taoka |
| 2011/0273564 | A1 | 11/2011 | Seger et al. |
| 2012/0026318 | A1 | 2/2012 | Huelsen et al. |
| 2012/0026330 | A1 | 2/2012 | Huelsen et al. |
| 2012/0169877 | A1* | 7/2012 | Heenan ............... B60S 1/0822 348/148 |
| 2013/0027557 | A1* | 1/2013 | Hirai ............... B60S 1/0844 348/148 |
| 2014/0029008 | A1 | 1/2014 | Hirai et al. |
| 2014/0303853 | A1* | 10/2014 | Itoh ............... B60R 11/04 701/49 |
| 2015/0034827 | A1 | 2/2015 | Kroekel et al. |
| 2015/0276982 | A1 | 10/2015 | Kroekel et al. |
| 2015/0321644 | A1 | 11/2015 | Kosubek et al. |
| 2016/0305873 | A1 | 10/2016 | Bix |

FOREIGN PATENT DOCUMENTS

| | | |
|---|---|---|
| DE | 102010028347 | 11/2011 |
| EP | 1 580 092 | 9/2005 |
| EP | 1 923 695 | 5/2008 |
| JP | 2010-096604 A | 4/2010 |
| JP | 2010-210374 A | 9/2010 |
| JP | 2010-223685 A | 10/2010 |
| WO | WO 2012/092911 | 7/2012 |
| WO | WO 2014/108123 | 7/2014 |

OTHER PUBLICATIONS

PCT International Preliminary Report on Patentability including English Translation of PCT Written Opinion of the International Searching Authority for International Application PCT/DE2014/200196, dated Jun. 7, 2016, 6 pages, International Bureau of WIPO, Geneva, Switzerland.

German Search Report for German Patent Application No. 10 2013 225 155.6, dated Dec. 16, 2013, 5 pages, Muenchen, Germany, with English translation, 5 pages.

* cited by examiner

ILLUMINATION FOR DETECTING RAINDROPS ON A PANE BY MEANS OF A CAMERA

FIELD OF THE INVENTION

The invention relates to a device for detecting rain on a pane by means of a lighting source and a camera.

BACKGROUND INFORMATION

In U.S. Pat. No. 7,259,367 B2, rain sensing by means of a camera is proposed, said rain sensing providing extensive lighting of the passing-through window of the camera aperture angle with the pane by means of an infrared diode. The camera focus is set to almost infinite and can thus be simultaneously used for driver assistance applications. Due to the imaging on the remote range raindrops are only noticeable as disturbances in the image, which are detected by complex differential measurements of the images recorded with infrared light pulsed or modulated in synchronization with the pixel clock.

A device and a method for detecting rain are described in WO 2012/092911 A1. A camera is disposed behind a pane, in particular in the interior of a vehicle behind a windshield, and focused onto a remote region that lies in front of the pane. A lighting source for generating at least one light beam that is directed at the pane directs the at least one light beam towards the pane such that at least one beam that is reflected from the outer face of the pane impinges on the camera as an external light reflex or external reflex. The light quantity of the at least one beam or light reflex that impinges on the camera can be measured by the camera. One or more light-emitting diodes optionally with a light guide or a light band are indicated as the lighting source. If the aperture angle of the illumination is large enough, the lighting source can also be located inside the camera, e.g. on a circuit board of the camera system.

The sensitivity of the rain detection hereby substantially depends on the configuration of the illumination.

SUMMARY OF THE INVENTION

An object of at least one embodiment of this invention is to indicate optimized illumination for camera-based rain detection, which guarantees high sensitivity.

The invention is based on the following basic considerations: the sensitivity of the rain detection depends on the lighting intensity and the area of the detection area on the windshield. An area corresponding to the image of the LEDs reflected on the windshield is covered with LEDs as the lighting source. This covered area is frequently not sufficient for efficient rain detection. The use of a light guide is, in addition, associated with a loss of the light intensity emitted by the lighting source.

A device for detecting rain on a pane according to the invention comprises a camera, a lighting source for emitting light and a diffusion element. The light emitted by the lighting source emerges as a light sheet from the diffusion element. The camera, the lighting source and the diffusion element are designed and arranged in such a way that the camera can detect a signal from the light or an imaging of the light sheet which is emitted by the lighting source, impinges through the diffusion element on the pane and is reflected by the pane. In particular, in this case, the signal detected by the camera or the light sheet(s) correlate(s) with light from the lighting source, which is reflected or scattered at the inner face or outer face of the pane and/or at the raindrop.

The diffusion element can also be described as a diffuser and can, in particular, be a diffusion filter or a diffusion layer. The light emitted by the lighting source, e.g. a row of light-emitting diodes, is advantageously dispersed by the diffusion element, which results in a uniformly illuminated exit face of the diffusion element, i.e. in the formation of a light sheet.

Diffusion elements are available in differing densities and with different dispersion angles (angle at which the intensity scattered is half the maximum intensity). Diffusion elements having a higher density (of diffusive/dispersing components) produce a greater dispersion which is associated with a greater loss of transmitted light. The greater dispersion results in a greater detection area of the pane being illuminated. The dispersion angle of different diffusion elements is also variable. A greater angle also allows a larger detection area, but weakens the light intensity.

As a rule, selecting a suitable diffusion element requires a reasonable compromise between transmission losses or reduction of intensity and the size of the detection area.

The configuration and arrangement of the diffusion element advantageously takes account of these relationships.

The camera preferably comprises an image sensor, for example a CCD or CMOS sensor, and a lens or imaging system for focusing electromagnetic radiation from one or more areas onto the image sensor.

The lighting source can, in particular, be configured as one or more organic light-emitting diodes (OLEDs).

The lighting source generates uniformly flat illumination (light sheet) of an area of the pane, together with the diffusion element.

Rain is preferably detected on the outer face of the pane in that the camera is arranged behind the pane and is focused onto a remote region in front of the pane.

The advantage of the device according to the invention is that inexpensive lighting is used, which makes it possible to detect rain in a sound and reliable manner. Both the material and the production costs for a device according to the invention are low compared to known camera-based devices with comparably varied areas of application and comparable effectiveness or sensitivity of the rain detection.

The camera, the lighting source and the diffusion element are advantageously designed and arranged in such a way that the camera can detect a first mirror image of the light sheet reflected at the inner face of the pane and a second mirror image of the light sheet reflected at the outer face of the pane. In designing the elements of the device, properties of the pane such as e.g. angle of inclination, refractive index and thickness should, in particular, be taken into consideration.

In this case, the camera, the lighting source and the diffusion element are preferably designed and arranged in such a way that the first and the second mirror images which can be detected by the camera do not overlap with one another, they can be adjacent to one another in this case. The first mirror image is not dependent on the presence of raindrops in the illuminated area of the pane, whilst the second mirror image is modified or attenuated if raindrops are present in the illuminated area of the pane, as parts of the light intensity are decoupled from the pane by the raindrops and are not reflected to the camera.

According to an advantageous embodiment, the light sheet is limited by an aperture formed at or on or in front of the diffusion element. The aperture can be formed by means of a black or non-reflective and impermeable limiting device on the exit face of the diffusion element. In particular, the aperture can be formed as a seal between the diffusion element and a receiving device for the diffusion element. As a consequence, it is possible to limit or adjust the light sheet.

In a preferred embodiment, the diffusion element is a diffusion film. Diffusion films can be used inexpensively in an extremely wide range of configurations.

The camera is advantageously focused by means of a lens onto a remote region, so that the mirror image(s) of the light sheet is/are shown as (a) blurred image(s) by the camera. As a result, the camera can be used as a multifunctional sensor for one or more additional driver assistance functions which are based on an evaluation of the remote region imaged in a focused manner such as e.g. Lane Departure Warning (LDW), Lane Keeping Assistance/System (LKA/LKS), Traffic Sign Recognition (TSR), Intelligent Headlamp Control (IHC), Forward Collision Warning (FCW), Adaptive Cruise Control (ACC), parking assistance and Emergency Brake Assist (EBA) or Emergency Steering Assist (ESA).

According to a preferred embodiment, the lighting source is arranged in a housing and the diffusion element is arranged in a recess of the housing. The housing can in particular be produced from metal. The aperture can be formed from a seal between the diffusion element and the recess of the housing.

The lighting source is advantageously arranged on a circuit board, wherein the circuit board is an integral part or carrier of the camera electronics. The circuit board can, in addition, be arranged inside the housing.

The camera advantageously comprises a view funnel or a view shield or a lens hood, which particularly restricts the field of vision of the camera (downwards) and ideally minimizes stray and scattered light reflexes. The diffusion element is arranged on the view funnel or is integrated into the view funnel. In order to achieve a compact design of the camera with integrated lighting, the lighting source can preferably be arranged under the view funnel. To this end, the diffusion element can advantageously be integrated into the view funnel in such a way that it "replaces" the view funnel in this area. Alternatively, the view funnel can have an area made of material which is permeable to light and the diffusion film can, in particular, be arranged thereon.

BRIEF DESCRIPTION OF THE DRAWINGS

The invention will be explained in more detail below, with reference to figures and embodiment examples, wherein.

DETAILED DESCRIPTION OF EXAMPLE EMBODIMENTS OF THE INVENTION

Figure 1:
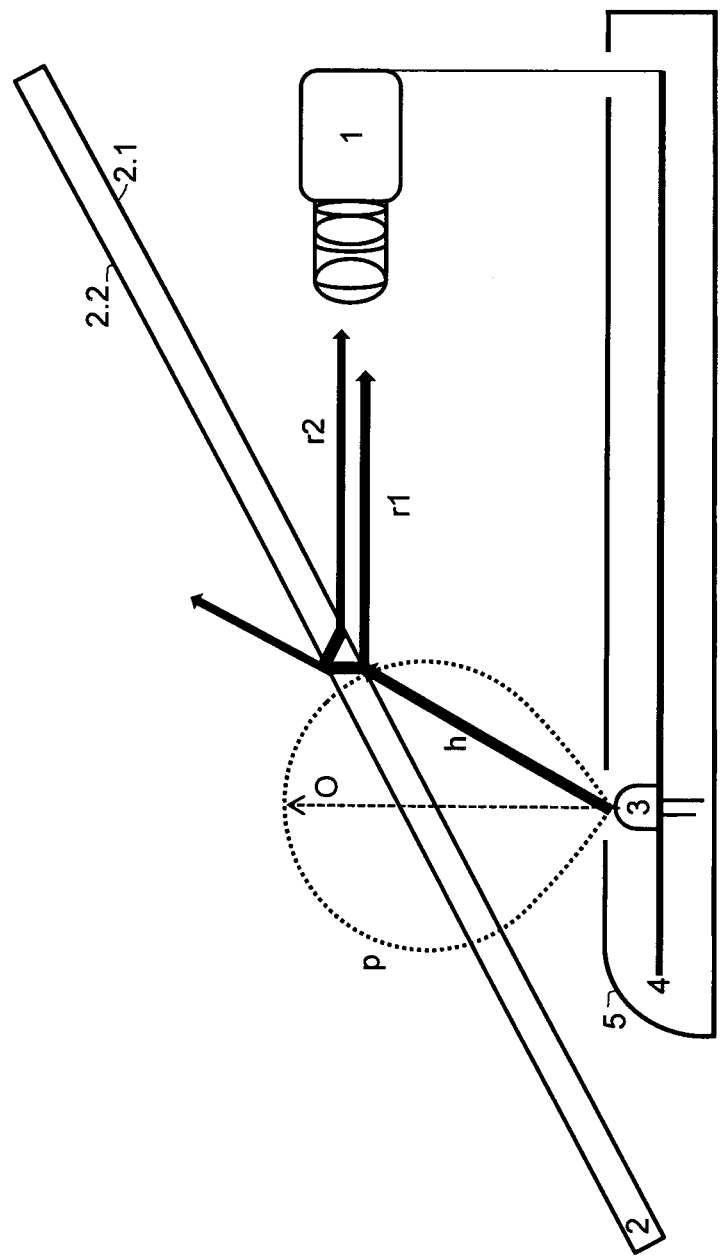
FIG. 1 schematically shows the basic principle of a possible arrangement of the lighting source, pane and camera for detecting rain (longitudinal section)

FIG. 1 shows a longitudinal section of a camera focused on the remote region together with a lens (1) and a lighting source (3) which emits light (o, p, h) onto a windshield (2) of a vehicle, which is essentially comparable with an embodiment example of WO 2012/092911 A1. The LED lighting source (3) emits light in a particular distribution (p), in this case with a beam angle or a full width at half maximum (FWHM) of the beam angle distribution of 120° and a maximum intensity in the central beam direction (o).

The aperture angle of the lighting is so large that beams reflected from a beam direction (h) at the inner face (2.1) and outer face (2.2) of the pane impinge on the lens or the camera (1) as two spatially separated beams (r1, r2). Most of the light emitted by the LED lighting source (direction o) is, however, not reflected by the windshield (2) to the camera (1) and is lost for rain detection. Due to the focusing on the remote region, the boundary of the beam bundle is only shown as a blurred image by the camera (1). Both reflected beams (r1, r2) are sufficiently separated and their respective light reflexes can be measured with the camera (1).

The portion (r1) of the light beam (h) reflected at the air-pane interface (or inner face of the pane (2.1)) can serve as a reference beam. Of the portion which is transmitted into the pane, that portion is used as a measurement beam (r2) which is reflected at the pane-air/raindrop interface (or outer face of the pane (2.2)) and impinges on the camera (1). Not shown is that portion of the beam which is repeatedly reflected inside the pane (2) (on the pane-air inner face (2.1) after having been reflected at the pane-raindrops outer face (2.2)). The beam paths (h, r1, r2) and light distributions (o, p) are shown schematically.

If, in the event of rain, the outer face (2.2) of the windshield (2) is wetted, the majority of the light transmitted through the inner face (2.1) into the pane is decoupled, so that the reflected portion (r2) is weaker than it is in the case of a dry pane (not shown). The beam (r1) reflected from the inner face (2.1) is unaffected by wetting of the outer face of the pane (2.2).

By comparing the measured light reflexes of both beams (r1 to r2), the reduced signal in the event of rain can therefore be easily measured and a windshield wiper can be activated accordingly.

The lighting source (3) preferably comprises a plurality of LEDs having a wide beam angle which are arranged in a row, only one of which is shown in FIG. 1. The additional LEDs can, in particular, be arranged in a row perpendicular to the plane shown in FIG. 1. A plurality of LEDs is advantageous, in order to achieve sufficient illumination for detecting rain. The LEDs are, in particular, arranged as upwardly beaming SMD components on a circuit board (4). The circuit board (4) can advantageously be a printed circuit board (PCB) of the camera electronics, which is arranged inside a housing (5) in order to protect it against dirt, humidity and electromagnetic disturbances. The connecting line between the camera (1) and the circuit board (4) in FIG. 1 is only intended to illustrate the fact that the circuit board (5) is an integral part of the camera electronics.

The area of the windshield (2) illuminated by the LEDs, which can be used to detect rain, is very small, e.g. of the order of a few mm$^2$. Raindrops, which are located on the outer face of the pane, are only illuminated by LEDs in this (detection) area. The sensitivity of the rain detection depends on the light intensity and the size of the detection area on the windshield. With LEDs as a lighting source (3), the detection area corresponds to the mirror image which is generated by reflection of the LED emission surfaces at the pane. The (detection) area covered as a result is not sufficient for effective rain detection.

Figure 2:
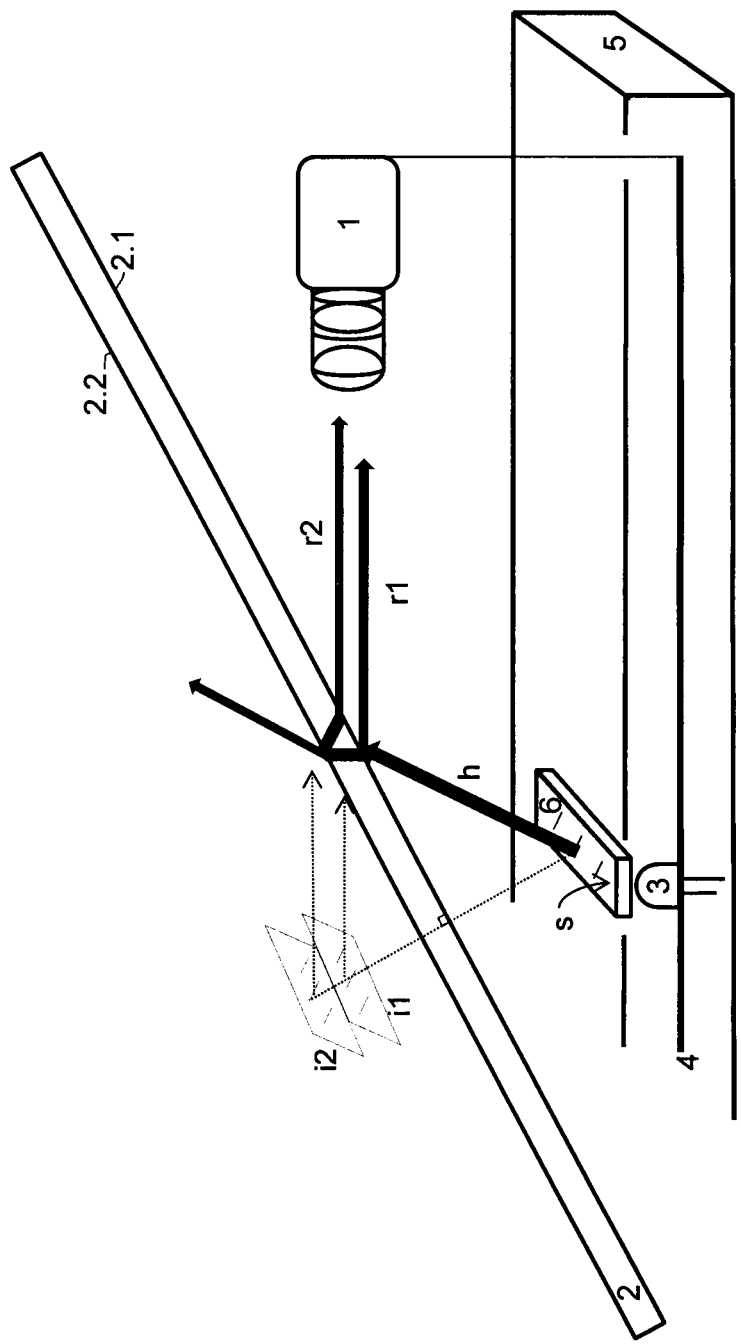
FIG. 2 shows an arrangement of a lighting source having a diffusion film, pane and camera for improved rain detection.

FIG. 2 shows an arrangement with a diffusion element (6) that is arranged above the lighting source (3). The lighting source (3) can, in particular, as described in connection with FIG. 1, be a plurality of LEDs arranged in a row. The diffusion element (6) can be a diffusion filter, a diffusion film or a diffusion layer. The light emitted by the lighting source (3) is dispersed by the diffusion element (6), which results in a uniformly illuminated exit face(s) of the diffusion element (light sheet).

Diffusion films have differing densities and scattering angles (angle at which the intensity scattered is half the maximum intensity). Diffusion films having a higher density (of diffusive/dispersing components) produce a greater dispersion which is associated with a greater loss of transmitted light. The greater dispersion results in a greater (detection) area of the windscreen (2) being illuminated. The scattering angle of different diffusion elements or films is also variable. A greater angle also allows a larger detection area, but weakens the light intensity.

In order to select a suitable diffusion element (6), a reasonable compromise has to be found between transmission losses or reduction of intensity and the size of the detection area. The intensity of the light from the light source (3), which can be detected by the camera (1) must, in this case, be sufficient for effective rain detection.

The mirror images or virtual images of the light sheet(s) produced by the inner face (i1) or outer face (i2) of the pane are visible to the camera (1).

Depending on the size of the illuminated area(s), the nature (refractive index and thickness) of the windshield, the angles between the illuminated area(s) and the windshield (2) as well as between the windshield (2) and the optical axis of the camera (1), overlapping of the first (i1) and second (i2) mirror images can occur in the camera image. This overlapping area cannot be used or can only be used with difficulty for effectively detecting rain. An overlapping of the first (i1) and second (i2) mirror images in the camera image should preferably be avoided.

Mounting a non-reflective and impermeable limiting device on the exit face of the diffusion element (6), in order to limit the illuminated face(s), represents one possible measure for avoiding this overlapping. Following the integration of the diffusion element (6) into an opening of the (metallic) housing (5), a black seal can be used to cover the surroundings of the diffusion element. As a result, an aperture is formed. The black seal prevents unwanted emission of stray light to the surroundings and unwanted stray light entering the diffusion element (6) from the surroundings of the same.

In order to adapt the device for various vehicles having various angles of inclination of the windshield (2), the diffusion element (6) can be arranged at a predefined, fixed angle and optionally also at a fixed, predefined distance from the respective windshield (2). To this end, the diffusion element (6) can, in particular, be arranged in such away that it is impinged on at a corresponding tilting angle. As a result, the covering or illumination of a similar detection area on the respective windshield (2) is possible for different windshield inclinations in different types of vehicles.

LIST OF REFERENCE NUMERALS

1 Camera
2 Windshield
2.1 Inner face of the windshield
2.2 Outer face of the windshield
3 Lighting source
4 Circuit board
5 Housing
6 Diffusion film
p Distribution of the light emitted by the lighting source
o Emission direction with the maximum intensity of the lighting source
h Lighting beam direction which is detected by the camera
r1 Portion of h, which is reflected at the inner face of the pane and detected by the camera
r2 Portion of h, which is reflected at the outer face of the pane and detected by the camera
s Light sheet or illuminated surface of the diffusion film
i1 Mirror image of the light sheet reflected at the inner face of the pane
i2 Mirror image of the light sheet reflected at the outer face of the pane

The invention claimed is:

1. A device for detecting raindrops on an outer face of a pane, comprising:
    a camera,
    an electronic circuit arrangement,
    a lighting source configured to emit light, and
    a diffusion element configured and arranged spaced apart from an inner face of the pane with a gap therebetween, so that the light emitted by the lighting source impinges on and diffuses through the diffusion element and emerges from the diffusion element as a diffuse light sheet that projects through the gap onto the inner face of the pane,
    wherein the camera, the lighting source and the diffusion element are configured and arranged so that the camera can detect a first mirror image of the diffuse light sheet reflected from the inner face of the pane and a second mirror image of the diffuse light sheet reflected from the outer face of the pane, and
    wherein the electronic circuit arrangement is connected to the camera and configured to detect the raindrops on the outer face of the pane based on signals output by the camera dependent on and in response to detecting the first mirror image and the second mirror image of the diffuse light sheet.

2. The device according to claim 1, wherein the first mirror image and the second mirror image do not overlap with one another.

3. The device according to claim 1, further comprising an aperture mounted at or on or in front of the diffusion element so as to limit the diffuse light sheet.

4. The device according to claim 1, wherein the diffusion element is a diffusion film.

5. The device according to claim 1, wherein the camera is focused by a lens onto a remote region in front of the outer face of the pane, so that the mirror images of the diffuse light sheet are detected as blurred images by the camera.

6. The device according to claim 1, further comprising a housing, wherein the lighting source is arranged inside the housing and the diffusion element is arranged in an opening in a wall of the housing.

7. The device according to claim 1, wherein the camera comprises a view funnel, and the diffusion element is arranged on the view funnel or is integrated into the view funnel.

8. The device according to claim 1, wherein the diffusion element has a rectangular light-emitting surface, and wherein the diffusion element and the lighting source are configured and arranged so that the diffuse light sheet is diffusely emitted uniformly over the rectangular light-emitting surface.

9. The device according to claim 1, wherein the lighting source comprises plural light emitting diodes arranged adjacent one another, and the diffusion element is a single one-piece diffusion element dimensioned, configured and arranged so that the light respectively emitted by each one of the plural light emitting diodes impinges on and diffuses through the single one-piece diffusion element to produce the diffuse light sheet that emerges from the single one-piece diffusion element.

10. The device according to claim 9, wherein the diffusion element and the plural light emitting diodes are configured and arranged so that the diffuse light sheet is diffusely emitted uniformly over an emitting surface area of the diffusion element that emits the diffuse light sheet.

11. The device according to claim 1, wherein a surface area of an exit face of the diffusion element that emits the diffuse light sheet is larger than a light-emitting surface area of the lighting source.

12. A device for detecting rain on an outer surface of a pane, comprising:
   an electrically-energizable light source that is configured to emit light;
   a diffusion element configured and arranged so that the light emitted by the light source is intercepted and diffused by the diffusion element and emerges from the diffusion element as a diffuse light sheet, and wherein the diffusion element is configured and arranged adjacent to and spaced apart from an inner surface of the pane with a gap therebetween so that a first light portion of the diffuse light sheet projects through the gap and impinges on and reflects from the inner surface of the pane, and so that a second light portion of the diffuse light sheet projects through the gap, impinges on the inner surface of the pane, is transmitted in the pane from the inner surface to the outer surface, and is reflected from the outer surface internally within the pane and then passes out of the pane through the inner surface;
   a camera that is configured and arranged adjacent to the inner surface of the pane so as to optically receive and electronically detect at least the second light portion and to produce a second signal dependent on the second light portion; and
   an electronic circuit arrangement that is connected to said camera so as to receive the second signal, and that is configured to detect the rain on the outer surface of the pane based on at least the second signal.

13. The device according to claim 12, wherein said camera is further configured and arranged so as to optically receive and electronically detect the first light portion and to produce a first signal dependent on the first light portion, and wherein said electronic circuit arrangement is configured to detect the rain on the outer surface of the pane by comparing the second signal to the first signal.

14. The device according to claim 13, wherein the first light portion represents a first reflection of the diffuse light sheet from the inner surface of the pane, the second light portion represents a second reflection of the diffuse light sheet from the outer surface of the pane, and said camera and said diffusion element are arranged so that the first reflection and the second reflection as detected by said camera do not overlap with one another.

15. The device according to claim 12, wherein said diffusion element has a rectangular light-emitting surface, and wherein said diffusion element and said light source are configured and arranged so that the diffuse light sheet is diffusely emitted uniformly over said rectangular light-emitting surface.

16. The device according to claim 12, wherein said light source comprises plural light emitting diodes arranged adjacent one another, and said diffusion element is a single one-piece diffusion element dimensioned, configured and arranged so that said single one-piece diffusion element intercepts and diffuses light respectively emitted by each one of said plural light emitting diodes to produce the diffuse light sheet that emerges from the single one-piece diffusion element.

17. The device according to claim 16, wherein said diffusion element and said plural light emitting diodes are configured and arranged so that the diffuse light sheet is diffusely emitted uniformly over an emitting surface area of said diffusion element that emits the diffuse light sheet.

18. The device according to claim 12, wherein the camera includes a lens configured to focus the camera onto a remote region in front of the outer surface of the pane, so that the camera is configured to detect a blurred image of the diffuse light sheet reflected from the inner surface of the pane in the first light portion and of the diffuse light sheet reflected from the outer surface of the pane in the second light portion.

* * * * *